US011442073B2

United States Patent
Crawford et al.

(10) Patent No.: US 11,442,073 B2
(45) Date of Patent: *Sep. 13, 2022

(54) METHODS AND SYSTEMS FOR MEASURING SEROTONIN IN A SAMPLE (71) Applicant: Laboratory Corporation of America Holdings, Burlington, NC (US)

(72) Inventors: Matthew Lee Francis Crawford, Mebane, NC (US); Yvonne Zamorano Wright, Burlington, NC (US); Russell Philip Grant, Chapel Hill, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/088,129

(22) Filed: Nov. 3, 2020

(65) Prior Publication Data

US 2021/0048445 A1 Feb. 18, 2021

Related U.S. Application Data

(63) Continuation of application No. 16/223,418, filed on Dec. 18, 2018, now Pat. No. 10,859,586, which is a continuation of application No. 15/059,957, filed on Mar. 3, 2016, now Pat. No. 10,191,070.

(60) Provisional application No. 62/127,590, filed on Mar. 3, 2015.

(51) Int. Cl.
| | |
|---|---|
| *G01N 33/483* | (2006.01) |
| *G01N 33/49* | (2006.01) |
| *G01N 33/68* | (2006.01) |
| *G01N 33/94* | (2006.01) |
| *G01N 30/72* | (2006.01) |
| *G01N 30/88* | (2006.01) |

(52) U.S. Cl.
CPC ........... *G01N 33/942* (2013.01); *G01N 33/49* (2013.01); *G01N 33/6848* (2013.01); *G01N 2030/8813* (2013.01); *G01N 2458/15* (2013.01); *G01N 2800/222* (2013.01)

(58) Field of Classification Search
CPC ....... G01N 2030/8813; G01N 2458/15; G01N 2800/222; G01N 33/48; G01N 33/49; G01N 33/6848; G01N 33/86; G01N 33/942; Y10T 436/145555; Y10T 436/17; Y10T 436/173845
USPC ............. 436/63, 69, 96, 106, 111, 161, 173; 422/70, 72, 73
See application file for complete search history.

(56) References Cited

U.S. PATENT DOCUMENTS

| | | | |
|---|---|---|---|
| 5,972,718 A | 10/1999 | Moghaddam et al. | |
| 7,468,358 B2 | 12/2008 | Kennedy et al. | |
| 9,851,367 B2 * | 12/2017 | Aster | G01N 33/6854 |
| 10,191,070 B2 * | 1/2019 | Crawford | G01N 33/942 |
| 10,859,586 B2 * | 12/2020 | Crawford | G01N 33/942 |
| 2002/0052017 A1 | 5/2002 | Hirowatari et al. | |
| 2006/0172438 A1 | 8/2006 | Milunic et al. | |
| 2009/0036405 A1 | 2/2009 | Kennedy | |
| 2012/0040373 A1 | 2/2012 | Ubeda | |
| 2012/0238030 A1 | 9/2012 | Rappold et al. | |
| 2014/0315223 A1 | 10/2014 | Curtis | |
| 2016/0231338 A1 | 8/2016 | Aster et al. | |
| 2016/0258969 A1 | 9/2016 | Crawford et al. | |
| 2021/0011035 A1 * | 1/2021 | Alkhalfioui | G01N 33/6893 |
| 2021/0325405 A1 * | 10/2021 | Padmanabhan | C12N 5/0644 |

FOREIGN PATENT DOCUMENTS

| | | |
|---|---|---|
| CN | 107430137 | 12/2017 |
| EP | 3265828 | 1/2018 |
| JP | 2002277461 | 9/2002 |
| JP | 2010534672 | 11/2010 |
| JP | 2014507657 | 3/2014 |
| JP | 2018-511043 | 4/2018 |
| JP | 2008518090 | 5/2019 |
| WO | WO 2012/109250 | 8/2012 |
| WO | WO 2014/195847 | 12/2014 |
| WO | WO 2016/141172 | 9/2016 |

OTHER PUBLICATIONS

Danaceau, J. et al., "A Liquid Chromatographic-Tandem Mass Spectrometric Method for the Analysis of Serotonin and Related Indoles in Human Whole Blood," J. Anal. Toxicol. 27:440-444 (2003).
Fouassier, M. et al., "Determination of serotonin release from platelets by HPLC and ELISA in the diagnosis of heparin-induced thrombocytopenia: comparison with reference method by [$^{14}$C]-serotonin release assay," J. Thromb. Haemost 4:1136-1139 (2006).
Koch, S. et al., "Development of a High-Pressure Liquid Chromatography Method for Diagnosis of Heparin-Induced Thrombocytopenia," Am. J. Clin. Pathol. 117:900-904 (2002).
Monaghan, P. et al., "Measurement of serotonin in platelet depleted plasma by liquid chromatography tandem mass spectrometry," J. Chromatogr. B. 877:2163-2167 (2009).
Sheridan, D. et al., "A Diagnostic Test for Heparin-Induced Thrombocytopenia," Blood 67(1):27-30 (1986).
International Patent Application No. PCT/US2016/020660, Search Report and Written Opinion dated May 17, 2016.
Peaston, B., "Tandem Mass Spectrometry in Clinical Diagnostics," Chromsystems Instruments & chemicals GmbH, Munich, Germany (8 pgs.) (2009).
Linkins, L. et al., "Treatment and Prevention of Heparin-Induced Thrombocytopenia," Chest 141(2)(Suppl):e495s-e530S (2012).
Watson, H. et al., "Guidelines on the diagnosis and management of heparin-induced thrombocytopenia: second edition," British J Haematol. 159:528-540 (2012).
Warkentin, T. et al., "Quantitative interpretation of optical density measurements using PF4-dependent enzyme-immunoassays," J. Thromb. Haemost. 6:1304-1312 (2008).

(Continued)

*Primary Examiner* — Maureen Wallenhorst
(74) *Attorney, Agent, or Firm* — Kilpatrick Townsend & Stockton LLP (57) ABSTRACT

Disclosed are methods and systems for measuring serotonin in a sample using liquid chromatography and mass spectrometry.

25 Claims, 4 Drawing Sheets

(56) References Cited

OTHER PUBLICATIONS

Warkentin, T. et al., "Laboratory testing for heparin-induced thrombocytopenia: a conceptual framework and implications for diagnosis," J. Thromb. Haemost. 9:2498-2500 (2011).
Moore, J. et al., "An algorithm for resolving 'indeterminate' test results in the platelet serotonin release assay for investigation of heparin-induced thrombocytopenia," J. Thromb. Haemost. 6:1595-1597 (2008).
Sono-Koree, N.K. et al., "High-Pressure Liquid Chromatography is a Robust Method for Performing the Serotonin Release Assay and Correlates Well with the Radioactivity Method," University of Utah School of Medicine, Department of Pathology (2011 poster presentation at XXIII Congress of the International Society on Thrombosis and Haemostasis; Jul. 23-28, 2011, Kyoto, Japan).
"Serotonin Release Assay," BloodCenter of Wisconsin (May 2012).
Warkentin, T. et al., "Spontaneous heparin-induced thrombocytopenia syndrome: 2 new cases and a proposal for defining this disorder," Blood 123(23):3651-3654 (2014).
Tan, C. et al., "Evaluating Heparin-Induced Thrombocytopenia: The Old and the New," Semin. Thromb. Hemost. 38:135-143 (2012).
Price, E. et al., "Laboratory testing for heparin-induced thrombocytopenia is inconsistent in North America: A survey of North American specialized coagulation laboratories," Thromb. Haemost. 98:1357-1361 (2007).
Prechel, M. et al., "Activation of platelets by heparin-induced thrombocytopenia antibodies in the serotonin release assay is not dependent on the presence of heparin," J. Thromb. Haemost. 3:2168-2175 (2005).
Szeitz et al., "A Validated Assay to Quantitate Serotonin in Lamp Plasma Using Ultrahigh-Performance Liquid Chromatography-tandem Mass Spectrometry: Applications With LC/MS3," Anal. Bioanal. Chem. 406(20):5055-5059 (2014).
Warkentin, T. et al., "The use of well-characterized sera for the assessment of new diagnostic enzyme-immunoassays for the diagnosis of heparin-induced thrombocytopenia," J. Thromb. Haemost. 8:216-218 (2010).
Bearcroft, C.P. et al., "Determination of 5-Hydroxytryptamine, 5-Hydroxyindoleacetic Acid and Tryptophan in Plasma and Urine by HPLC with Fluorimetric Detection," Biomedical Chromatography 9:23-27 (1995).
European Patent Application No. 16 711 432.1, Office Action dated Oct. 30, 2018.
U.S. Appl. No. 15/059,957, Office Action dated May 22, 2018.
U.S. Appl. No. 15/059,957, Notice of Allowance dated Sep. 28, 2018.
U.S. Appl. No. 16/223,418, Office Action dated Apr. 24, 2020.
CN 201680011384.4, Office Action, dated Mar. 16, 2020, 22 pages.
CN 201680011384.4, Office Action, dated Dec. 18, 2018, 20 pages.
CN 201680011384.4, Office Action, dated Sep. 2, 2019, 28 pages.
JP 2017-543765, English translation of Office Action dated Nov. 27, 2019, 20 pages.
JP 2017-543765, Office Action, dated Jul. 17, 2020, 6 pages.
EP 21169228.0, Extended European Search Report, dated Sep. 6, 2021, 11 pages.
De Jong, W. et al., "Automated Mass Spectrometric Analysis of Urinary and Plasma Serotonin", Anal. Bioanal. Chem., 396(7):2609-2616 (2010).
U.S. Appl. No. 16/223,418, Notice of Allowance, dated Aug. 13, 2020, 8 pages.
JP 2017-543765, Office Action, dated Dec. 23, 2020, 3 pages.
PCT/US2016/020660, International Preliminary Report on Patentability, dated Sep. 14, 2017, 9 pages.
CA 2,973,201, Office Action, dated Nov. 30, 2021, 5 pages.
JP 2017-543765, Office Action, dated Jun. 1, 2022, 11 pages.

\* cited by examiner

METHODS AND SYSTEMS FOR MEASURING SEROTONIN IN A SAMPLE

CROSS REFERENCE TO RELATED APPLICATION

This application is a continuation of U.S. patent application Ser. No. 16/223,418, filed Dec. 18, 2018, now U.S. Pat. No. 10,859,586, issued Dec. 8, 2020, which is a continuation of U.S. patent application Ser. No. 15/059,957, filed Mar. 3, 2016, now U.S. Pat. No. 10,191,070, issued Jan. 29, 2019, which claims the benefit of U.S. Provisional Application No. 62/127,590, filed Mar. 3, 2015, the entirety of all of which is hereby incorporated herein by reference.

FIELD OF INVENTION

The present invention relates to methods and systems for indirectly measuring heparin induced autoantibodies through the measurement of serotonin in a sample. In certain embodiments, the invention provides methods and systems for measuring serotonin or stable labeled serotonin released from donor platelets, challenged with a specimen from a patient suspected of having heparin induced thrombocytopenia (HIT), using liquid chromatography and mass spectrometry.

BACKGROUND

Heparin-induced thrombocytopenia (HIT) is a potentially catastrophic, antibody-mediated complication of heparin therapy caused by immunization against platelet factor 4 (PF4) complexed with heparin or other polyanions. HIT antibodies bind to PF4/heparin complexes on the platelet surface, resulting in platelet activation that leads to a platelet count decrease that can be accompanied by life-threatening thrombosis. This prothrombotic disorder can produce devastating thromboembolic complications, including ischemic limb necrosis, pulmonary embolism, myocardial infarction, and stroke.

Moderate thrombocytopenia is common in the clinical settings where heparin is administered and most cases are not caused by HIT. Differentiation of HIT from other potential causes of thrombocytopenia is a difficult diagnostic component in the evaluation of heparinized, thrombocytopenic patients and relies on a combination of a clinical assessment and laboratory investigation. Prompt diagnosis and management is critical to minimizing the risk of life-threatening thrombosis. Patients diagnosed with or suspected of suffering HIT must be taken off heparin and transitioned to an alternative non-heparin anticoagulant as quickly as possible.

The laboratory investigation of HIT is challenging and requires correlation between clinical symptoms and laboratory assays. The most common assay performed is a serologic assay that detects the presence of HIT antibodies without regard for their functional ability. Several serologic assays which are relatively easy to perform are available commercially and these assays are highly sensitive. The results of these assays have excellent negative predictive values and a negative result can be used to exclude HIT in all but the most compelling clinical circumstances. However, these assays suffer from low specificity and frequently give positive results in the absence of clinical HIT. A positive result, especially of low titer, does not differentiate between pathogenic antibodies and clinically irrelevant antibodies.

Another approach to measure HIT is to use an assay that measures platelet function, i.e., a functional assay. Functional assays that measure platelet activation by HIT antibodies in the presence of heparin are considered gold standard diagnostic laboratory tests due to their ability to detect the patient's underlying procoagulable state in those with true HIT. One functional assay is the measurement of serotonin released by platelets, i.e, the serotonin release assay (SRA). In this assay, sera from patients with heparin-induced thrombocytopenia (HIT) initiate platelet aggregation and secretion at therapeutic concentrations of heparin, but not at high concentrations of heparin. Generally, such assays measure radiolabeled serotonin released from platelets. However, due to complexity of performance, functional assays that use washed platelets are not widely available. Furthermore, serotonin release assays using washed platelets are typically performed using platelets that have been incubated with radiolabeled serotonin, and thus are accompanied by the drawbacks associated with using radioactive material.

SUMMARY

Described herein are methods and systems for indirectly measuring heparin induced antibodies through the measurement of serotonin in a sample.

In certain embodiments, the invention provides methods and systems for measuring serotonin or stable labeled serotonin released from donor platelets challenged with a specimen from a patient suspected of having heparin induced thrombocytopenia (HIT) using liquid chromatography and mass spectrometry. The methods and systems of the invention have advantages over other methods in that the assay does not require the use of radiolabeled serotonin. In addition, the method incorporates an LC-MS/MS system that results in a more sensitive, highly accurate test for HIT. The method can be useful for other conditions and diseases associated with abnormal donor platelet activation. The present invention may be embodied in a variety of ways.

In at least one aspect, the invention provides methods for determining the presence or amount of released serotonin and/or stable labeled serotonin in a sample, the methods comprising: providing a sample comprising a biological sample, donor platelets, and heparin; incubating the sample for a period of time to release serotonin from the donor platelets; chromatographically separating serotonin from other components in the incubated sample using liquid chromatography; and analyzing the chromatographically separated serotonin by mass spectrometry to determine the presence or amount of released serotonin in the sample relative to the total amount of serotonin available within the donor platelets. Further embodiments of these methods are described in detail below.

In another aspect, the invention provides methods for determining the presence or amount of released serotonin in a sample, the methods comprising: providing a sample comprising a biological sample, heparin, and serotonin-incubated platelets; incubating the sample for a period of time to release serotonin from the platelets; chromatographically separating serotonin from other components in the incubated sample using liquid chromatography; and analyzing the chromatographically separated serotonin by mass spectrometry to determine the presence or amount of released serotonin in the combined sample relative to the total amount of serotonin available within the donor platelets. Further embodiments of these methods are described in detail below.

In another aspect, the invention provides methods for determining the presence or amount of released stable isotopically labeled serotonin in a sample, the methods comprising: providing a sample comprising a biological sample, heparin, and stable isotopically labeled serotonin-incubated platelets; incubating the sample for a period of time to release stable isotopically labeled serotonin from the platelets; chromatographically separating stable isotopically labeled serotonin from other components in the incubated sample using liquid chromatography; and analyzing the chromatographically separated stable isotopically labeled serotonin by mass spectrometry to determine the presence or amount of released stable isotopically labeled serotonin in the sample relative to the total amount of stable isotopically labeled serotonin available within the donor platelets. Further embodiments of these methods are described in detail below.

In another aspect, the invention provides methods of generating a report useful for diagnosing a disease or condition associated with abnormal donor platelet activation, the methods comprising: providing a sample comprising a biological sample, donor platelets, and heparin; incubating the sample for a period of time to release serotonin or stable labeled serotonin from the donor platelets; chromatographically separating serotonin from other components in the incubated sample using liquid chromatography; analyzing the chromatographically separated serotonin by mass spectrometry to determine the amount of released serotonin in the sample relative to the total amount of serotonin available within the donor platelets; and generating a report that recites the percentage release of serotonin in the sample. Further embodiments of these methods are described in detail below.

In another aspect, the invention provides systems for determining the presence or amount of serotonin in a sample, the systems comprising a station for providing a sample comprising a biological sample, donor platelets, and heparin; a station for incubating the sample for a period of time to release serotonin from the donor platelets; a station for chromatographically separating serotonin from other components in the incubated sample using liquid chromatography; and a station for analyzing the chromatographically separated serotonin by mass spectrometry to determine the presence or amount of released serotonin in the sample relative to the total amount of serotonin available within the donor platelets. Further embodiments of these systems are described in detail below.

Further aspects of the invention are described in detail below.

BRIEF DESCRIPTION OF THE DRAWINGS

The present application includes the following figures. The figures are intended to illustrate certain embodiments and/or features of the invention, and to supplement any description(s) of the invention. The figures do not limit the scope of the invention, unless the written description expressly indicates that such is the case.

DETAILED DESCRIPTION

The following description recites various aspects and embodiments of the present invention. No particular embodiment is intended to define the scope of the invention. Rather, the embodiments merely provide non-limiting examples various methods and systems that are at least included within the scope of the invention. The description is to be read from the perspective of one of ordinary skill in the art; therefore, information well known to the skilled artisan is not necessarily included.

Various abbreviations may be used in the application. In most, if not all, instances, the meanings of such abbreviations are known to those of skill in the art. These abbreviations include the following abbreviations, whose meanings are provided.
HPLC=high performance liquid chromatography
LOQ=limits of quantification
LLOQ=lower limit of quantification
ELISA=enzyme linked immunoassay
ESI=electrospray ionization
ULOQ=upper limit of quantification
(LC)-MS/MS=liquid chromatography hyphenated to tandem mass spectrometry Definitions The following terms, unless otherwise indicated, shall be understood to have the following meanings:

As used herein, the terms "a," "an," and "the" can refer to one or more unless specifically noted otherwise.

Throughout this application, the term "about" is used to indicate that a value includes the inherent variation of error for the device, the method being employed to determine the value, or the variation that exists among the study subjects.

As used herein, the term "biomarker" is any biomolecule that may provide biological information about the physiological state of an organism. In certain embodiments, the presence or absence of the biomarker may be informative. In other embodiments, the level of the biomarker may be informative. A biomarker may be a neurotransmitter, such as serotonin, or a metabolite of a neurotransmitter.

As used herein, the terms "subject," "individual," and "patient" are used interchangeably. The use of these terms does not imply any kind of relationship to a medical professional, such as a physician.

As used herein, the term "biological sample" is used to refer to any fluid or tissue that can be isolated from an individual. For example, a biological sample may be whole blood, plasma, serum, other blood fraction, urine, cerebrospinal fluid, tissue homogenate, saliva, amniotic fluid, bile, mucus, peritoneal fluid, lymphatic fluid, perspiration, tissues, tissue homogenate, and the like.

As used herein, the term "sample" is used to refer to a mixture containing a biological sample, donor platelets, and heparin. The sample may contain additional components.

As used herein, the phrase "liquid chromatography" or "LC" is used to refer to a process for the separation of one or more molecules or analytes in a sample from other analytes in the sample. LC involves the slowing of one or more analytes of a fluid solution as the fluid uniformly moves through a column of a finely divided substance. The slowing results from the distribution of the components of the mixture between one or more stationery phases and the mobile phase. LC includes, for example, reverse phase liquid chromatography (RPLC) and high pressure liquid chromatography (HPLC).

As used herein, the term "separate" or "purify" or the like are not used necessarily to refer to the removal of all materials other than the analyte of interest from a sample matrix. Instead, in some embodiments, the terms are used to refer to a procedure that enriches the amount of one or more analytes of interest relative to one or more other components present in the sample matrix. In some embodiments, a "separation" or "purification" may be used to remove or decrease the amount of one or more components from a sample that could interfere with the detection of the analyte, for example, by mass spectrometry.

As used herein, the term "mass spectrometry" or "MS" analysis refers to a technique for the identification and/or quantitation of molecules in a sample. MS includes ionizing the molecules in a sample, forming charged molecules; separating the charged molecules according to their mass-to-charge ratio; and detecting the charged molecules. MS allows for both the qualitative and quantitative detection of molecules in a sample. The molecules may be ionized and detected by any suitable means known to one of skill in the art. The phrase "tandem mass spectrometry" or "MS/MS" is used herein to refer to a technique for the identification and/or quantitation of molecules in a sample, wherein multiple rounds of mass spectrometry occur, either simultaneously using more than one mass analyzer or sequentially using a single mass analyzer. As used herein, a "mass spectrometer" is an apparatus that includes a means for ionizing molecules and detecting charged molecules.

As used herein, "electrospray ionization" or "ESI" refers to a technique used in mass spectrometry to ionize molecules in a sample while avoiding fragmentation of the molecules. The sample is dispersed by the electrospray into a fine aerosol. The sample will typically be mixed with a solvent, usually a volatile organic compound (e.g., methanol or acetonitrile) mixed with water. The aerosol is then transferred to the mass spectrometer through a capillary, which can be heated to aid further solvent evaporation from the charged droplets.

As used herein, a "quadrupole analyzer" is a type of mass analyzer used in MS. It consists of four circular rods (two pairs) that are set highly parallel to each other. The quadrupole analyzer is the component of the instrument that organizes the charged particles of the sample based on their mass-to-charge ratio. One of skill in the art would understand that use of a quadrupole analyzer can lead to increased specificity of results. One pair of rods is set at a positive electrical potential and the other set of rods is at a negative potential. To be detected, an ion must pass through the center of a trajectory path bordered and parallel to the aligned rods. When the quadrupoles are operated at a given amplitude of direct current and radio frequency voltages, only ions of a given mass-to-charge ratio will resonate and have a stable trajectory to pass through the quadrupole and be detected. As used herein, "positive ion mode" refers to a mode wherein positively charged ions are detected by the mass analyzer, and "negative ion mode" refers to a mode wherein negatively charged ions are detected by the mass analyzer. For "selected ion monitoring" or "SIM," the amplitude of the direct current and the radio frequency voltages are set to observe only a specific mass.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 µm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns" or "preparative columns," which typically are used to separate or extract retained materials from non-retained materials to obtain a "purified" sample for further purification or analysis. In some embodiments, the extraction column is a functionalized silica or polymer-silica hybrid or polymeric particle or monolithic silica stationary phase, such as a Poroshell SBC-18 column.

As used herein, the term "heparin treatment" refers to a treatment regimen that includes administration of a heparin drug to a subject (e.g., a human subject). The term "heparin drug" refers to various heparins and heparin derivatives as known to those of skill in the art, including, but not limited to, heparin, unfractionated heparin, and low molecular weight heparins, including enoxaparin, dalteparin, and tinzaparin. Such drugs can be used for the treatment of various conditions, including conditions requiring anticoagulants (e.g., atrial fibrillation, pulmonary embolism, deep vein thrombosis, venous thromboembolism, congestive heart failure, stroke, myocardial infarction, and genetic or acquired hypercoagulability).

Methods for Determining the Presence or Amount of Serotonin in a Sample

In at least one aspect, the invention provides methods for determining the presence or amount of released serotonin in a sample.

Serotonin is a marker of platelet activation. Serum from patients with HIT initiates platelet aggregation and secretion at therapeutic concentrations of heparin, but not at high concentrations of heparin. The methods or assays described herein measure serotonin release from donor platelets in the presence of a biological sample, such as a patient's serum or plasma, at two heparin concentrations, i.e., a low heparin concentration and a high heparin concentration. The serotonin release is determined by measuring the amount of released serotonin and comparing the released serotonin to the total serotonin available in the donor platelets. The total serotonin available in the donor platelets can include endogenous serotonin and can also include serotonin spiked in with the platelets. In the embodiments of the invention described herein, the sample is incubated in the presence of donor platelets and heparin for a period of time to release serotonin from the donor platelets. Serotonin can then be chromatographically separated from other components in the incubated sample using liquid chromatography. In some embodiments of the methods described herein, the chromatographically separated serotonin is analyzed by mass spectrometry to determine the amount of released serotonin in the sample. Also, in certain embodiments, a report reciting the percentage release of serotonin in the sample is generated.

Figure 2:
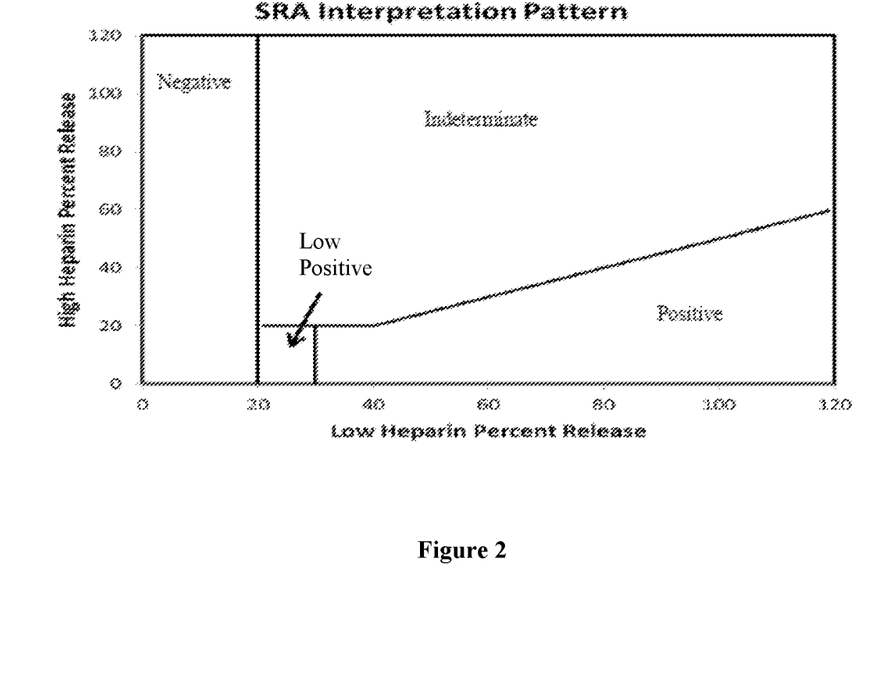
FIG. 2 is a graphical depiction of the serotonin release assay interpretation pattern for use in diagnosing heparin-induced thrombocytopenia.

An example and graphical depiction of an assay according to some embodiments of the methods described herein is shown in FIG. 2. As illustrated in FIG. 2, a sample is labelled as "negative," "intermediate," "low positive" or "positive" according to the criteria described herein, which are based on the relationships of measurements for the percent release of serotonin at a low concentration of heparin and at a high concentration of heparin. A "positive" result supports a diagnosis of HIT. A "negative" results argues against a diagnosis of HIT, but may not completely exclude it. A "low positive" or "indeterminate" result should be interpreted in in conjunction with other HIT assays and the context of all the clinical information including the platelet count, the type of heparin administered, the duration of heparin exposure, previous heparin exposure and any thrombotic history.

In one aspect, the method for determining the presence or amount of released serotonin in a sample comprises (a) providing a sample comprising a biological sample, donor platelets, and heparin; (b) incubating the sample for a period of time to release serotonin from the donor platelets; (c) chromatographically separating serotonin from other components in the incubated sample using liquid chromatography; and (d) analyzing the chromatographically separated serotonin by mass spectrometry to determine the presence or amount of released serotonin in the sample relative to the total amount of serotonin available within the donor platelets.

As known to those of skill in the art, sera from patients with heparin-induced thrombocytopenia (HIT) initiates platelet aggregation and secretion at therapeutic concentrations of heparin, but not at high concentrations of heparin. Thus, the method described herein measures the release of serotonin from platelets at two heparin concentrations (i.e., a low heparin concentration and a high heparin concentration), since sera from patients with HIT cause the release of serotonin at low, therapeutic concentration of heparin, but not at high concentrations of heparin. This assay has an advantage over other methods in that the assay does not require the use of radiolabeled serotonin. In addition, the method incorporates an LC-MS/MS system that results in a more sensitive, highly accurate test for HIT. The method can be useful for other conditions and diseases associated with abnormal donor platelet activation. The steps of the methods are further described below.

Providing a Sample

These methods include providing a sample comprising a biological sample, donor platelets, and heparin. In this context, the term "providing" is to be construed broadly. The term is not intended to refer exclusively to a subject who provided a biological sample. For example, a technician in an off-site clinical laboratory can be said to "provide" the sample, for example, as the sample is prepared for purification by chromatography.

The sample is not limited to any particular sample type. The sample contains a biological sample, donor platelets, and heparin, but, in general, also includes other components. In some embodiments, the sample is a sample that has been processed and prepared for purification by chromatography. Such processing may be useful for optimizing the effectiveness of subsequent purification steps. Such processing methods are well known to those of skill in the art.

The invention is not limited to any particular means of sample handling. In some embodiments, it may be useful to separate the sample into two or more fractions prior to purification by chromatography. In some such embodiments, two or more of such fractions may be prepared differently, for example, to help improve the sensitivity or selectivity of the separation for a particular column chemistry. In some embodiments, the method includes preparing a single sample for repeat injections across multiple liquid chromatography systems. The invention is not limited to any particular sample size.

The sample comprises a biological sample. In such embodiments, the biological sample may also include other components, such as solvents, buffers, anticlotting agents, and the like. In some embodiments, the biological sample can be one or more of whole blood, plasma, serum, urine, cerebrospinal fluid, tissue homogenate, saliva, amniotic fluid, bile, mucus, peritoneal fluid, or lymphatic fluid. In some embodiments, the biological sample is serum or plasma. In some embodiments, the biological sample is obtained from a drug-treated subject. For example, the biological sample can be obtained from a heparin-treated subject or a subject treated with a heparin analogue or derivative. In some embodiments, the biological sample is obtained from a subject previously treated with heparin, unfractionated heparin, and low molecular weight heparins, including enoxaparin, dalteparin, and tinzaparin. In some embodiments, the biological sample is obtained from a subject having or at risk for developing a disease or condition associated with abnormal platelet activation. For example, the biological sample can be obtained from a subject at risk for developing heparin-induced thrombocytopenia. A subject at risk for developing heparin-induced thrombocytopenia can include subjects previously or currently treated with heparin. The invention is not limited to any particular volume of biological sample. In some embodiments, the biological sample is at least about 1-100 µL, at least about 10-75 µL, or at least about 15-50 µL in volume. In certain embodiments, the biological sample is at least about 20 µL in volume.

The sample additionally includes donor platelets. In some embodiments, the donor platelets are obtained from at least one healthy subject (e.g., a subject that does not have heparin-induced thrombocytopenia or a condition or disease associated with abnormal platelet activation). For example, the donor platelets can be obtained from plasma from patients according to the method described below in Example 1. In some embodiments, the donor platelets are washed and/or purified prior to use in the sample. It has been found that in certain cases, a limiting aspect to the assay is the endogenous amount of serotonin present in the platelets. Thus, in some embodiments, the donor platelets are incubated with serotonin prior to the providing step so as to increase the amount of serotonin present in the platelets that is available for release in the incubating step. In some embodiments, the donor platelets are incubated with labeled serotonin. Labeled serotonin can be used as an additional method for measuring the released serotonin. The label on the serotonin can include a stable isotope, such as deuterium, carbon-13, nitrogen-15, and/or oxygen-18. For example, the donor platelets in the sample can be incubated with carbon-13 labeled serotonin, nitrogen-15 labeled serotonin, oxygen-18 labeled serotonin, deuterium labeled serotonin, or combinations of these labels prior to the providing step. In some embodiments, the amount of serotonin or stable labeled serotonin that can be used for incubating with donor platelets can range from 50 ng/mL to 500 ng/mL (e.g., from 75 ng/mL to 400 ng/mL or from 150 ng/mL to 300 ng/mL). The invention is not limited to any particular volume of donor platelets. Optionally, the donor platelets are provided in the form of a suspension in a buffer (e.g., an aqueous buffer). The buffer can include calcium ions ($Ca^{2+}$) and at least one enzyme. In some embodiments, the enzyme is apryase, a calcium-activated plasma membrane bound enzyme, which prevents adenosine diphosphate (ADP) accumulation. In some embodiments, the donor platelet suspension is at least about 25-250 µL, at least about 35-200 µL, at least about 45-150 µL, or at least about 50-100 µL in volume. In certain embodiments, the donor platelet suspension is at least about 75 µL in volume.

The sample also includes heparin. As described above, the assay is performed using two concentrations of heparin. In some samples, heparin is provided in a low concentration. A low concentration of heparin can include heparin provided in an amount of from 0.001 to 1 U/mL, from 0.005 to 0.5 U/mL, or from 0.01 to 0.25 U/mL. In some embodiments, heparin is provided in an amount of 0.2 U/mL. In other samples, heparin is provided in a high concentration. A high concentration of heparin can include heparin provided in an amount of from 50 to 1000 U/mL, from 75 to 750 U/mL, or from 100 to 500 U/mL. In some embodiments, heparin is provided in an amount of 100 U/mL. The invention is not limited to any particular volume of heparin. In some embodiments, the high concentration of heparin or the low concentration of heparin is provided to the sample in an amount of at least about 0.1-25 µL, at least about 0.5-20 µL, or at least about 1-15 µL in volume. In certain embodiments, the biological sample is at least about 10 µL in volume.

Serotonin Release from Donor Platelets

The methods comprise incubating the sample for a period of time to release serotonin from the donor platelets. In some embodiments, the incubating step is performed at room temperature. The incubating step can be performed for at least 30 minutes (e.g., at least 40 minutes, at least 45 minutes, at least 50 minutes, at least 55 minutes, or at least 60 minutes). The incubating step can additionally include applying mechanical action to facilitate serotonin release. Such mechanical action can include agitation, vibration, shaking, and the like. In some embodiments, the incubating step can further include adding a reagent to the sample to end the serotonin release reaction. The reagent to end the reaction can be referred to herein as a "stop reagent." In some embodiments, the stop reagent includes a chelating agent that binds divalent ions, such as calcium ($Ca^{2+}$). For example, the stop reagent can include ethylenediaminetetraacetic acid (EDTA).

In some embodiments of the invention, the incubated sample can undergo one or more processing steps before chromatographic separation. For example, in some embodiments, the incubated sample can be evaporated. Then the resulting residue can be reconstituted in a solvent system. Any suitable solvent system can be used for reconstituting the residue. In some embodiments, the solvent system is a solvent system that is compatible with chromatographic separation. In some embodiments, the solvent system for reconstitution includes, but is not limited to, water, methanol, or mixtures thereof.

In some embodiments of the invention, the incubated sample can be partially purified prior to the chromatographic separation steps. For example, the incubated sample can be centrifuged and the supernatant can be collected to partially purify the sample. In some embodiments, an internal standard, as further described herein, can be added prior to the chromatographic separation steps.

Chromatographically Separating Serotonin

The methods may comprise chromatographically separating serotonin from other components in the incubated sample using liquid chromatography. The invention is not limited to any particular manner of performing liquid chromatography. In general, the chromatographic separation step may include using at least one liquid chromatography (LC) column. In some embodiments, multiple LC columns are used, such as two or more, or three or more, or four or more LC columns. In some such embodiments two, three, four, five, six, eight, or ten LC columns are used. In some such embodiments, two or more of these LC columns are arranged parallel to each other, and are connected inline to the same mass spectrometer.

The invention is not limited to any particular types of columns. Any column suitable for the separation of serotonin can be used. In some embodiments, one or more analytical columns are used. In some such embodiments, one or more reverse phase columns are used. In some embodiments, the method employs two or more reverse phase columns in parallel, which are connected inline to the same mass spectrometer.

Further, the invention is not limited to any particular mobile phase. Any suitable mobile phase can be used, as long as the mobile phase is suitable for use with a particular LC column and for chromatographically separating serotonin in the LC column. In some embodiments, the mobile phase is a polar solvent system. The polar solvent system can include one or more polar solvents, including but not limited to water, methanol, acetonitrile, or a mixture of two or more of the foregoing. In some such embodiments, the mobile phase employs a gradient, such that the relative ratios of two or more solvents are varied over time.

As noted above, two or more LC columns (e.g., reverse phase columns) can be used in parallel and connected inline to the same mass spectrometer, e.g., to improve throughput. In some such embodiments, a serotonin-containing sample (i.e., the incubated sample)) is introduced to the two or more LC columns at different times. In some embodiments, the introduction of the test sample to the two or more LC columns is staggered, meaning that there is a pre-determined time interval separating the introduction of sample to two or more LC columns. Appropriate time intervals can be selected based on various factors, including the elution time, column chemistries, and the potential need to avoid interfering with the analysis of serotonin eluted from one or more of the other LC columns.

In some embodiments of the invention, one or more LC columns can be placed in series with another column. For example, in some embodiments, suitable guard columns can be employed. A guard column is a column, typically mounted upstream from the analytical column, used to protect the analytical column from chemical impurities in samples. Those of skill in the art are able to select appropriate guard columns for use in the present methods. In some embodiments, a guard column is placed in parallel with another LC column, and both the guard column and the LC column are reverse phase columns. Such series of two or more columns can also be arranged in parallel, such that there are two or more series of columns operating in parallel, where each series contains two or more columns.

Analyzing the Serotonin

The methods comprise analyzing the chromatographically separated serotonin by mass spectrometry to determine the presence or amount of released serotonin relative to the total amount of serotonin available within the donor platelets. In some embodiments, two or more of the LC columns feed into the same mass spectrometer. In some further embodiments, three or more of the LC columns feed into the same mass spectrometer. In some embodiments, the mass spectrometer is part of a combined LC-MS system.

The invention is not limited to any particular type of mass spectrometer. Any suitable mass spectrometer can be used.

In some embodiments, the method employs a tandem mass spectrometer. In some such embodiments, analyzing serotonin can include, ionizing serotonin or a labeled serotonin, analyzing the ionized serotonin or labeled serotonin, fragmenting the serotonin or labeled serotonin into two or more product ions, and analyzing the product ions. The invention is not limited to a mass spectrometer using any particular ionization methods. Any suitable ionization can be used. Suitable ionization methods include, but are not limited to photoionization, electrospray ionization, atmospheric pressure chemical ionization, atmospheric pressure photoionization, and electron capture ionization. In embodiments that employ fragmenting, any suitable fragmentation technique can be used. Suitable techniques include, but are not limited to, collision induced dissociation, electron capture dissociation, electron transfer dissociation, infrared multiphoton dissociation, radiative dissociation, electron-detachment dissociation, and surface-induced dissociation.

In some embodiments, the tandem mass spectrometer is a MDS-Sciex API5000 triple quadrupole mass spectrometer. In some embodiments, the tandem mass spectrometer has an atmospheric pressure ionization source, and the analyzing step comprises an ionization method selected from the group consisting of photoionization, electrospray ionization (ESI), atmospheric pressure chemical ionization (APCI), electron capture ionization, electron ionization, fast atom bombardment/liquid secondary ionization (FAB/LSI), matrix assisted laser desorption ionization (MALDI), field ionization, field desorption, thermospray/plasmaspray ionization, and particle beam ionization. The ionization method may be in positive ion mode or negative ion mode. The analyzing step may also include multiple reaction monitoring or selected ion monitoring (SIM), and the two or more biomolecules are analyzed simultaneously or sequentially. In some embodiments, the analyzing step uses a quadrupole analyzer. In some embodiments, the mass spectrometer is a triple quadrupole mass spectrometer. In embodiments that include a triple quadrupole mass spectrometer, the analyzing step can include detecting intact serotonin ion in the first quadrupole; fragmenting intact serotonin ion in the second quadrupole to yield one or more serotonin fragment ions; and detecting the one or more serotonin fragment ions in the third quadrupole.

In some embodiments, the analyzing step comprises ionizing the chromatographically separated serotonin to produce one or more serotonin ions having a mass/charge ratio comprising at least one of a precursor ion of 160.1± 0.5, or a product ion of 115.1± 0.5, 132.1± 0.5, 105.1± 0.5, or 89.1± 0.5. In some embodiments, the analyzing step includes simultaneously measuring multiple transitions, as listed above, for serotonin. Transition ratio measurements provide confidence in the measurement of the reported result. The ratios of two transitions are compared to the average ratio of the calibrators.

The methods, in some embodiments, include using an internal standard. In such embodiments, the internal standard can be introduced at any suitable point prior to the chromatographic separation step. Any suitable internal standard can be used. In some embodiments, the internal standard is a stable isotopically-labeled form of serotonin. In some such embodiments, the internal standard is labeled by carbon-13, nitrogen-15, and/or deuterium. The internal standard can be, for example, tetradeuterated serotonin (i.e., serotonin-d4).

In some embodiments, the method can be used to determine the presence or absence of serotonin or labeled serotonin in a sample. In other embodiments, the method is used to determine the amount of serotonin or labeled serotonin in a sample.

In some embodiments, the method is not limited by any lower-limit and/or upper-limit of detection. In some embodiments, the methods can be used to measure the serotonin or labeled serotonin in a sample (e.g., the incubated sample) at concentrations that range from 1 ng/mL to 1000 ng/mL, or from 5 ng/mL to 750 ng/mL, or from 10 ng/mL to 500 ng/mL.

As discussed above, it has been found that in certain cases, a limiting aspect to the assay is the endogenous amount of serotonin present in the platelets. Therefore, in another aspect, the invention provides methods for determining the presence or amount of released serotonin in a sample where platelets are "spiked" with serotonin. Specifically, serotonin or a labeled serotonin can be incubated with donor platelets prior to the providing step. Spiking platelets is beneficial in that the resulting assay has an increased analytical sensitivity, the resulting assay can determine potential errors in existing, commercially available serotonin release assays, and the assay can effectively differentiate false positives and negatives. The benefits of spiking platelets include an increased analytical sensitivity of the assay.

In one embodiment, the methods for determining the presence or amount of released serotonin in a sample comprises: (a) providing a sample comprising a biological sample, heparin, and serotonin-incubated platelets; (b) incubating the sample for a period of time to release serotonin from the platelets; (c) chromatographically separating serotonin from other components in the incubated sample using liquid chromatography; and (d) analyzing the chromatographically separated serotonin by mass spectrometry to determine the presence or amount of released serotonin in the sample relative to the total amount of serotonin available within the donor platelets. In another embodiment, the methods for determining the presence or amount of released serotonin in a sample comprises: (a) providing a sample comprising a biological sample, heparin, and stable isotopically labeled serotonin-incubated platelets; (b) incubating the sample for a period of time to release stable isotopically labeled serotonin from the platelets; (c) chromatographically separating stable isotopically labeled serotonin from other components in the incubated sample using liquid chromatography; and (d) analyzing the chromatographically separated stable isotopically labeled serotonin by mass spectrometry to determine the presence or amount of released stable isotopically labeled serotonin in the sample relative to the total amount of stable isotopically labeled serotonin available within the donor platelets.

The features and embodiments of all steps are described immediately above. As noted above, the stable isotopically labeled serotonin can be carbon-13 labeled serotonin, nitrogen-15 labeled serotonin, oxygen-18 labeled serotonin, deuterated serotonin, or combinations thereof.

Figure 1:
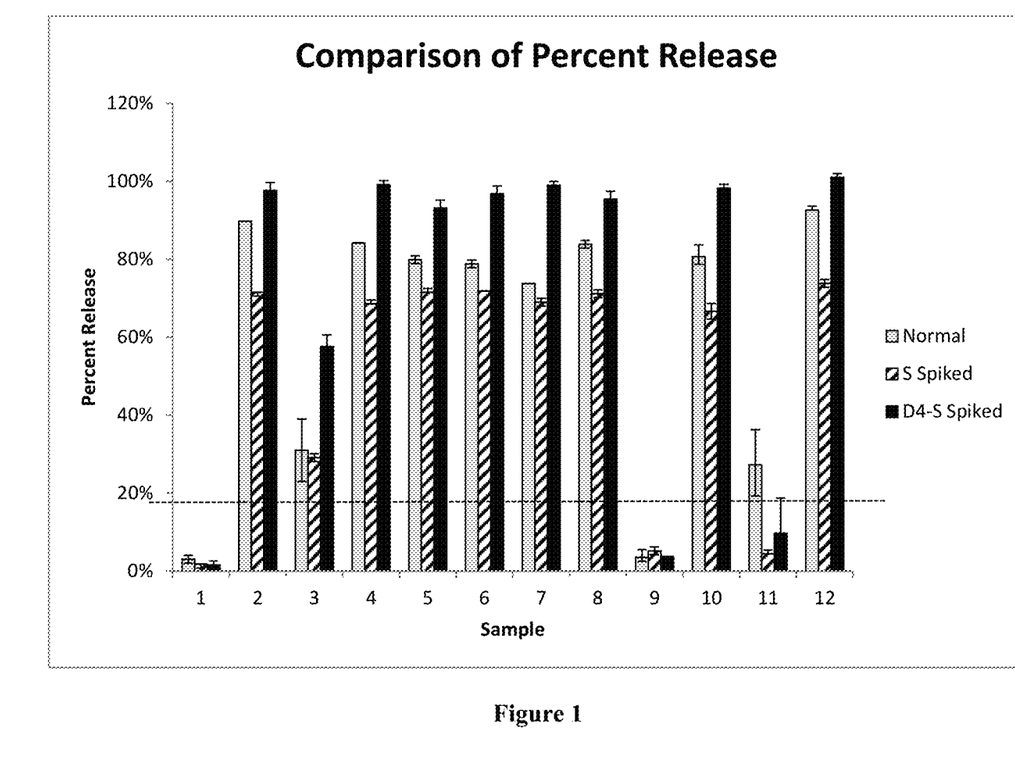
FIG. 1 is a graph comparing the percent releases for serotonin released from non-spiked platelets (Normal), serotonin released from serotonin spiked platelets (S spiked), and serotonin released from d4-serotonin spiked platelets (D4-S spiked). The dashed line represents 20% release compared to the total serotonin available in donor platelets.

A comparison of percent release of serotonin using the three methods (i.e., non-spiked, which is labeled as normal; serotonin spiked, which is labeled as S-Spiked; and labeled serotonin spiked, which is labeled as D4-S Spiked) is shown, for exemplary purposes, in FIG. 1. FIG. 1 represents 12 samples assayed using native serotonin, spiked serotonin, and D4 spiked serotonin platelets and subsequent release measurements assayed in triplicate (see precision bars). Samples 1 and 9 were HIT negative, thus consistent with all methods, Sample 11 was borderline low positive/indeterminate, all other samples were HIT positive. FIG. 1 shows the clinical agreement between the non-spiked, serotonin spiked, and labeled serotonin spiked approaches in the measurement of HIT.

Methods of Generating Reports

In another aspect, the invention provides methods of generating a report useful for diagnosing a disease or condition associated with abnormal platelet activation, the methods comprising: (a) providing a sample comprising a biological sample, donor platelets, and heparin; (b) incubating the sample for a period of time to release serotonin from the donor platelets; (c) chromatographically separating serotonin from other components in the incubated sample using liquid chromatography; (d) analyzing the chromatographically separated serotonin by mass spectrometry to determine the amount of released serotonin in the sample; and (e) generating a report that recites the percentage release of serotonin in the sample.

The features and embodiments of all steps except step (e) are described immediately above. As noted above, the method can employ more than one column, e.g., two or more columns in parallel connected inline to the same mass spectrometer.

The method further includes generating a report that recites the amount of serotonin (e.g., released serotonin) in the sample. The amount of released serotonin can be conveyed as the percent release. In some embodiments, this information can be used to determine the concentration of released serotonin in a biological sample compared to the total available serotonin in a donor sample. From such information, one could assess whether a subject has HIT.

The methods can include correlating the percent release of serotonin at a low concentration of heparin and at a high concentration of heparin to diagnose heparin-induced thrombocytopenia in a subject. The sample can be labeled as "negative," "low positive," "positive," or "indeterminate," as further described below. The assay measures serotonin release from donor platelets in the presence of patient's serum. The serotonin release is determined by measuring the amount of released serotonin and comparing the released serotonin to the total serotonin available in the donor platelets. The total serotonin available in the donor platelets can include endogenous serotonin and can also include serotonin spiked in with the platelets, as described herein.

A positive result requires >20% release in the presence of low dose (0.2 IU/mL) heparin and inhibition of release (reduction of 50% or more of the release measured with low dose heparin or less than 20%) in the presence of high dose (100 IU/mL) heparin.

A sample is labeled as "negative" if the percent release in the presence of low dose heparin is 0-20% and the percent release in the presence of high dose heparin is less than 20%. While these results argue against a diagnosis of heparin-induced-thrombocytopenia (HIT), they do not completely exclude the diagnosis.

A sample is labeled as "low positive" if the percent release in the presence of low dose heparin is 21-30% and the percent release in the presence of high dose heparin is less than 20%. While these results are positive, they fall just above the cut-off and should be interpreted in in conjunction with other HIT assays and the context of all the clinical information including the platelet count, the type of heparin administered, the duration of heparin exposure, previous heparin exposure and any thrombotic history.

A sample is labeled as "positive" if the percent release in the presence of low dose heparin is greater than or equal to 31% and the percent release in the presence of high dose heparin is less than 50% or the percent release of the low dose heparin or less than 20% of the total serotonin available within the donor platelets. The result supports a diagnosis of heparin-induced-thrombocytopenia (HIT).

A sample is labeled as "indeterminate" if the percent release in the presence of low dose heparin is greater than or equal to 20% and the percent release in the presence of high dose heparin is greater than or equal to 20%, unless the high dose heparin result is less than 50% of the low dose heparin. Although there was >20% serotonin release in the presence of low dose heparin, this reaction was not adequately inhibited by high dose heparin. While these results are not consistent with a diagnosis of heparin-induced-thrombocytopenia (HIT), they do not completely exclude the diagnosis. The result should be interpreted in conjunction with other HIT assays, and the context of all the clinical information including the platelet count, the type of heparin administered, the duration of heparin exposure, previous heparin exposure and any thrombotic history.

FIG. 2 provides a graphical representation of the relationships of measurements for the percent release of serotonin at a low concentration of heparin and at a high concentration of heparin to diagnose heparin-induced thrombocytopenia in a subject.

Systems for Determining the Presence or Amount of Serotonin in a Sample

In another aspect, the invention provides systems for determining the presence or amount of serotonin in a sample, the systems comprising: (a) a station for providing a sample comprising a biological sample, donor platelets, and heparin; (b) a station for incubating the sample for a period of time to release serotonin from the donor platelets; (c) a station for chromatographically separating serotonin from other components in the incubated sample using liquid chromatography; and (d) a station for analyzing the chromatographically separated serotonin by mass spectrometry to determine the presence or amount of released serotonin in the sample.

In another aspect, the invention provides systems for determining the presence or amount of serotonin in a sample, the systems comprising: (a) a station for providing a sample comprising a biological sample, serotonin-incubated platelets, and heparin; (b) a station for incubating the sample for a period of time to release serotonin from the donor platelets; (c) a station for chromatographically separating serotonin from other components in the incubated sample using liquid chromatography; and (d) a station for analyzing the chromatographically separated serotonin by mass spectrometry to determine the presence or amount of released serotonin in the sample.

In another aspect, the invention provides systems for determining the presence or amount of serotonin in a sample, the systems comprising: (a) a station for providing a sample comprising a biological sample, stable isotopically labeled serotonin-incubated platelets, and heparin; (b) a station for incubating the sample for a period of time to release stable isotopically labeled serotonin from the donor platelets; (c) a station for chromatographically separating stable isotopically labeled serotonin from other components in the incubated sample using liquid chromatography; and (d) a station for analyzing the chromatographically separated stable isotopically labeled serotonin by mass spectrometry to determine the presence or amount of released stable isotopically labeled serotonin in the sample.

Such systems can include various embodiments and subembodiments analogous to those described above for methods of determining the presence or amount of serotonin in a sample.

These systems include various stations. As used herein, the term "station" is broadly defined and includes any suitable apparatus or collections of apparatuses suitable for carrying out the recited method. The stations need not be integrally connected or situated with respect to each other in any particular way. The invention includes any suitable arrangements of the stations with respect to each other. For example, the stations need not even be in the same room. In some embodiments, the stations are connected to each other in an integral unit.

The systems can include a station for providing a sample comprising a biological sample, donor platelets, and heparin using the methods described herein. The systems can include a station for incubating the sample for a period of time to release serotonin from the donor platelets using the methods described herein. The systems can include a station for chromatographically separating serotonin from other components in the incubated sample using liquid chromatography using the methods described herein. The systems can include a station for analyzing the chromatographically separated serotonin by mass spectrometry to determine the presence or amount of released serotonin in the sample using the methods described herein. The systems can include a station for generating a report useful for diagnosing a disease or condition associated with abnormal platelet activation using the methods described herein.

Non-Limiting Embodiments

Non-limiting embodiments include:

1. A method for determining the presence or amount of released serotonin in a sample, the method comprising:
providing a sample comprising a biological sample, donor platelets, and heparin;
incubating the sample for a period of time to release serotonin from the donor platelets;
chromatographically separating serotonin from other components in the incubated sample using liquid chromatography; and
analyzing the chromatographically separated serotonin by mass spectrometry to determine the presence or amount of released serotonin in the sample.

2. The embodiment of paragraph 1, wherein the biological sample is a serum sample or a plasma sample.

3. The embodiment of paragraphs 1 and/or 2, wherein the biological sample is obtained from a heparin-treated subject.

4. The embodiment of any of paragraphs 1-3, wherein the biological sample is obtained from a subject suspected of having heparin-induced thrombocytopenia.

5. The embodiment of any of paragraphs 1-4, wherein the donor platelets are obtained from at least one presumed healthy subject.

6. The embodiment of any of paragraphs 1-5, wherein the donor platelets in the sample are washed and partially purified.

7. The embodiment of any of paragraphs 1-6, wherein the incubating step is performed at room temperature.

8. The embodiment of any of paragraphs 1-7, wherein the incubating step is performed for at least 30 minutes.

9. The embodiment of any of paragraphs 1-8, wherein the heparin in the providing step is present in an amount of from 0.001 to 1 U/mL.

10. The embodiment of any of paragraphs 1-8, wherein the heparin in the providing step is present in an amount of from 50 to 1000 U/mL.

11. The embodiment of any of paragraphs 1-10, further comprising contacting the incubated sample with an internal standard prior to the chromatographically separating step.

12. The embodiment of 11, wherein the internal standard is a stable isotopically-labeled form of serotonin.

13. The embodiment of paragraph 12, wherein the stable isotopically-labeled form of serotonin comprises deuterium labeled serotonin, carbon-13 labeled serotonin, nitrogen-15 labeled serotonin, oxygen-18 labeled serotonin, or combinations thereof.

14. The embodiment of paragraph 13, wherein the internal standard is serotonin-d4.

15. The embodiment of any of paragraphs 1-14, wherein the donor platelets in the providing step were incubated with serotonin prior to the providing step.

16. The embodiment of any of paragraphs 1-14, wherein the donor platelets in the providing step were incubated with deuterium labeled serotonin, carbon-13 labeled serotonin, nitrogen-15 labeled serotonin, oxygen-18 labeled serotonin, or combinations thereof prior to the providing step.

17. The embodiment of any of paragraphs 1-16, further comprising partially purifying the incubated sample prior to the chromatographically separating step.

18. The embodiment of paragraph 17, wherein the partially purifying step comprises centrifuging the incubated sample.

19. The embodiment of any of paragraphs 1-18, wherein using liquid chromatography includes using analytical liquid chromatography.

20. The embodiment of paragraph 19, wherein using analytical liquid chromatography includes using a reverse phase column.

21. The embodiment of any of paragraphs 1-20, wherein using liquid chromatography includes using at least one column.

22. The embodiment of any of paragraphs 1-21, wherein using liquid chromatography includes using two or more liquid chromatography columns in parallel, where the two or more liquid chromatography columns are connected inline to a single mass spectrometer.

23. The embodiment of paragraph 22, wherein using two or more liquid chromatography columns in parallel includes introducing the incubated sample to the two or more liquid chromatography columns at staggered times.

24. The embodiment of any of paragraphs 1-23, wherein the analyzing step includes ionizing serotonin using an ionization technique selected from the group consisting of: electrospray ionization, atmospheric pressure chemical ionization, and atmospheric pressure photoionization.

25. The embodiment of any of paragraphs 1-24, wherein the analyzing step includes detecting serotonin using a quadrupole mass spectrometer.

26. The embodiment of paragraph 25, wherein the quadrupole mass spectrometer is a triple quadrupole mass spectrometer.

27. The embodiment of paragraph 26, wherein the analyzing step includes: detecting intact serotonin ion in the first quadrupole; fragmenting intact serotonin ion in the second quadrupole to yield one or more serotonin fragment ions; and detecting the one or more serotonin fragment ions in the third quadrupole.

28. The embodiment of any of paragraphs 1-27, wherein the analyzing step comprises ionizing the chromatographically separated serotonin to produce one or more serotonin ions having a mass/charge ratio comprising at least one of a precursor ion of $160.1 \pm 0.5$, or a product ion of $115.1 \pm 0.5$, $132.1 \pm 0.5$, $105.1 \pm 0.5$, or $89.1 \pm 0.5$.

29. A method for determining the presence or amount of released serotonin in a sample, the method comprising:
providing a sample comprising a biological sample, heparin, and serotonin-incubated platelets;
incubating the sample for a period of time to release serotonin from the platelets;
chromatographically separating serotonin from other components in the incubated sample using liquid chromatography; and
analyzing the chromatographically separated serotonin by mass spectrometry to determine the presence or amount of released serotonin in the sample relative to the total amount of serotonin available within the donor platelets.

30. A method for determining the presence or amount of released stable isotopically labeled serotonin in a sample, the method comprising:
providing a sample comprising a biological sample, heparin, and stable isotopically labeled serotonin-incubated platelets;
incubating the sample for a period of time to release stable isotopically labeled serotonin from the platelets;
chromatographically separating stable isotopically labeled serotonin from other components in the incubated sample using liquid chromatography; and
analyzing the chromatographically separated stable isotopically labeled serotonin by mass spectrometry to determine the presence or amount of released stable isotopically labeled serotonin in the sample relative to the total amount of isotopically labeled serotonin available within the donor platelets.

31. The embodiment of paragraph 30, wherein the stable isotopically labeled serotonin is deuterium labeled serotonin, carbon-13 labeled serotonin, nitrogen-15 labeled serotonin, oxygen-18 labeled serotonin, or combinations thereof prior to the providing step.

32. A method of generating a report useful for diagnosing a disease or condition associated with abnormal platelet activation, the method comprising:
(a) providing a sample comprising a biological sample, donor platelets, and heparin;
(b) incubating the sample for a period of time to release serotonin from the donor platelets;
(c) chromatographically separating serotonin from other components in the incubated sample using liquid chromatography;
(d) analyzing the chromatographically separated serotonin by mass spectrometry to determine the amount of released serotonin in the sample relative to the total amount of serotonin available within the donor platelets; and
(e) generating a report that recites the percentage release of serotonin in the sample.

33. The embodiment of paragraph 33, wherein the disease or condition is heparin-induced thrombocytopenia.

34. A system for determining the presence or amount of serotonin in a sample, the system comprising:
(a) a station for providing a sample comprising a biological sample, donor platelets, and heparin;
(b) a station for incubating the sample for a period of time to release serotonin from the donor platelets;
(c) a station for chromatographically separating serotonin from other components in the incubated sample using liquid chromatography; and
(d) a station for analyzing the chromatographically separated serotonin by mass spectrometry to determine the presence or amount of released serotonin in the sample relative to the total amount of serotonin available within the donor platelets.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Serotonin Release Assay (SRA) for Use in the Diagnosis of Heparin-Induced Thrombocytopenia (HIT)

Serotonin was measured by mass spectrometric detection after isotope dilution and chromatographic separation. Stable labeled isotope for serotonin was added as the internal standard to sample aliquots. After the addition of internal standard in precipitating solution to sample aliquots, the samples were mixed, centrifuged, further diluted with ethyl acetate and then injected onto a LC-MS/MS system. An MDS-Sciex API5500 triple quadrupole mass spectrometer, operating in positive ion electrospray ionization mode was used for detection. Quantification of analyte and internal standards were performed in selected reaction monitoring mode (SRM). The back-calculated amount of the serotonin in each sample was determined from a calibration curve generated by spiking known amounts of purified serotonin into blank charcoal stripped serum from 1-1000 ng/mL. Percent serotonin release was calculated using total serotonin in platelets and serotonin release in the presence of patient serum and donor platelets.

Specimens

A recommended sample was 0.5 mL-1.0 mL serum or plasma. Plasma was collected from adult or pediatric human donors using a tube containing acid citrate dextrose (ACD). Serum was collected from adult or pediatric human patients using a standard sampling tube.

Equipment & Materials

The following supplies and instruments were used: manual pipettes with tips or validated automated pipetting system; Class A volumetric pipettes and flasks; assorted glass reagent bottles; vortex mixer (VWR; Radnor, Pa.); 5804-R Centrifuge with microplate rotors or equivalent (Eppendorf; Hamburg, Germany); Easy Pierce Heat Sealing Foil (Fisher Healthcare; Waltham, Mass.); Thermo Manual Heat Sealer ALPS25 or equivalent (Thermo Scientific; Waltham, Mass.); 96-well polypropylene deep well plates (Phenomenex; Torrance, Calif.); API 5000 Tandem Mass Spectrometer and Turbo V™ Ion Source with Electrospray (Sciex; Toronto, Canada); Aria Transcend TX4 System consisting of 8 1200SL Series Binary Pumps and 4 1200 Series Vacuum Degasser (Thermo-Fisher; Waltham, Mass.); HTS Twin PAL System Autosampler (CTC Analytics AG, Switzerland); Analyst version 1.4 or greater (Applied Biosystems; Foster City, Calif.); Aria OS version 1.6 or greater (Thermo-Fisher; Waltham, Mass.); Ascentis Express HILIC column, 3 cm×3.0 mm, 2.7 µm (Sigma-Aldrich; St. Louis, Mo.); heat plate (Fisher Scientific); glass Pasteur pipette (Fisher Scientific; Waltham, Mass.); polystyrene microtiter plate (Thermo Scientific; Waltham, Mass.); titer plate shaker (Thermo Scientific; Waltham, Mass.); Big Shot II hybridization oven (Boekel; Feasterville, Pa.); pH meter (Metier Toledo; Columbus, Ohio); and a sonicator (Gen-Probe; San Diego, Calif.).

Reagents

The following reagents were used: D4-Serotonin (CDN Isotopes; Quebec, Canada); Serotonin Hydrochloride (Sigma; St. Louis, Mo.); Sodium Hydroxide 10N (Fisher Scientific; Waltham, Mass.); Hydrochloric Acid (Fisher Scientific; Waltham, Mass.); CSS Mass Spec Gold (Golden West Biologicals; Temecula, Calif.); Alpha-D-Glucose (Aldrich; St. Louis, Mo.); Calcium Chloride (Sigma; St. Louis, Mo.); Magnesium Chloride (Sigma; St. Louis, Mo.); Sodium Chloride (Sigma; St. Louis, Mo.); HEPES (Sigma; St. Louis, Mo.); Sodium Phosphate (mono) (Sigma; St. Louis, Mo.); Potassium Chloride (Sigma; St. Louis, Mo.); Apyrase (Sigma; St. Louis, Mo.); Citrate-dextrose solution (Sigma; St. Louis, Mo.); Heparin sodium salt (Sigma; St. Louis, Mo.); Optima Water HPLC Grade (Fisher Scientific; Waltham, Mass.); Formic Acid, >95% (Sigma-Aldrich; St. Louis, Mo.); Acetonitrile, HPLC Grade (Fisher Scientific; Waltham, Mass.); Methanol, HPLC Grade (Fisher Scientific; Waltham, Mass.); Ethyl Acetate (Fisher Scientific; Waltham, Mass.); Ethylenediaminetetraacetic acid (EDTA) (Fisher Scientific; Waltham, Mass.); and Phosphate Buffered Saline (PBS) (Sigma; St. Louis, Mo.).

The following solutions were prepared as the mobile phases for liquid chromatography, wash buffers, and reagents for use in the methods:

Needle Wash Solution 1 (Aqueous 0.1% Formic Acid): Formic acid (1 mL) was added to 999 mL of Type I Millipore water in a 1 L reagent bottle. The contents of the bottle were mixed well and stored at room temperature.

Needle Wash Solution 2 (Methanol): Methanol (1000 mL) was transferred to a glass bottle and stored at room temperature.

Pump A Mobile Phase (50:50 Acetonitrile: Ethyl Acetate): Acetonitrile (1000 mL) and 1000 mL ethyl acetate were added to a 2 L bottle and mixed. The mixture was stored at room temperature.

Pump B Mobile Phase (10 mM Ammonium Formate with 3% Formic Acid): Approximately 1.26 grams ammonium formate was weighed on an analytical balance and transferred to a Class A 2 L volumetric flask. The flask was filled halfway with Millipore water. Formic acid (60 mL) was added, followed by the appropriate amount of Millipore water, to bring the solution to 2 L. The solution was mixed well and stored at room temperature.

Solution 1 for Wash Buffer Prep: In a 1.0 liter volumetric flask was added 8.0 g NaCl, 0.2 g KCl, and 0.4 g $NaH_2PO_4$. The solution was brought to the desired volume with Optima water.

SRA Wash Buffer 1: To prepare 400 mL of Wash Buffer 1, two separate 200 mL flasks of Wash Buffer 1 were prepared. For a single 200 mL flask, the entire contents of a 500 unit Apyrase bottle, approximately 0.2 g glucose, and approximately 0.24 g HEPES were combined. The appropriate amount of Solution 1 was added to arrive at 200 mL. Both of the 200 mL flasks were combined, and the combined solution was adjusted to pH 6.3± 0.05 using 1N HCl or 1N NaOH. The solution was stored refrigerated.

SRA Wash Buffer 2: In a 500 mL flask were added approximately 0.1 g CaCl and 0.1 g MgCl, followed by the appropriate amount of Solution 1 to arrive at 500 mL. The pH of the solution was adjusted to 7.4± 0.05 using 1N HCl or 1N NaOH. The solution was stored refrigerated.

High Concentration Heparin Solution—1050 IU/mL: The amounts of components for the high concentration heparin solution were calculated based on the Certificate of Analysis (C of A) data for the particular heparin used, according to the formula shown below:

$$(\text{Amount weighed out}) \times (\# \text{ of } U/mg(C \text{ of } A)) = \text{Total } \# \text{ of Units}$$

$$(\text{Total \# of Units})/1050 IU/mL = X\ mL\ \text{Optima Water}$$

For example, if the amount of material weighed out was 111.48 mg and the C of A for the heparin used was 193 U/mg, then the total number of units was 21515.6 U and approximately 20.5 mL of Optima water was used. The solution was stored refrigerated.

Low Concentration Heparin Solution—2.1 IU/mL: The low concentration heparin solution was prepared from the high concentration (1050 IU/mL) solution. To prepare the low concentration heparin solution, 0.05 mL of the high concentration heparin (1050 IU/mL) was measured out and the solution was brought to a final volume of 25 mL using Optima water. The solution was stored refrigerated.

Working Internal Standard Solution: d4-Serotonin was weighed to create a top stock of 1 mg/mL in 50:50 MeOH:$H_2O$. The top stock (0.25 mL) was added to 1 Liter of 100% acetonitrile. The solution was stored refrigerated.

Phosphate Buffered Saline (PBS): To prepare the PBS solution, one pack of PBS was used per one liter of Millipore water. To prepare one liter of 0.5% EDTA in PBS, 5 g of EDTA was added to the PBS solution and the solution was sonicated for 15 minutes.

SRA Stop Reagent: The stop reagent for the serotonin release assay (SRA) was 0.5% EDTA in phosphate-buffered saline (PBS). To prepare the reagent, 5 g EDTA was added to a flask and PBS solution was added to arrive at a final volume of 1 Liter. The solution was stored at room temperature.

Calibration

Calibrators were prepared from a stock solution of serotonin (1 mg/mL) in methanol. Standards having the following concentrations (in ng/mL) were prepared: 1, 2, 10, 25, 100, 250, and 500 in charcoal stripped serum. Standards were stored for up to one year in capped tubes when stored at −70° C.

Quality Controls (QC's)

Analytical QC: Charcoal Stripped Serum and Pooled serum were screened prior to the quality control prep. All QC's were sub-aliquoted and stored at −70° C. To prepare QC1 (~3 ng/mL), 60 µL of Top Stock 3 was pipetted into a flask and the solution was brought to a final volume of 100 mL using charcoal stripped serum (CSS). To prepare QC2 (~200-400 ng/mL): 100 µL of Top Stock 4 and pipetted into a flask and the solution was brought to a final volume of 100 mL using charcoal stripped serum (CSS).

Biological QC: To prepare the Biological QC's, previously run HIT ELISA samples were reviewed. Samples previously analyzed by HIT ELISA with a result greater than or equal to 1.5 OD were selected and were run in QC Sample Prep Microtiter Plate. Samples with negative (≤20%) results were pooled together to create the Biological QC1 Negative. Samples with HIGH (≥75%) results were pooled together to create the Biological QC2 HIGH. All QC's were sub-aliquoted and stored at −70° C.

Donor Procedure

Platelet Washing Protocol for Donor Screening

Platelets were washed according to the following protocol for donor screening: Blood was drawn from donors into ACD tubes and the tubes were inverted to mix the contents (8-10 mls of platelets~four tubes per plate). The tubes were centrifuged at 1200 rpm for 10 minutes. Platelet rich plasma (PRP) was removed using glass Pasteur Pipettes with a small pipette bulb. Added ACD (111 μL) was added for every mL of plasma. The tubes were inverted to mix the contents. Using 16×100 polypropylene tubes, PRP tubes for the plate QCs were combined. The PRP was centrifuged at 2400 rpm for 15 minutes and a line was drawn on the outside of the tube to indicate the liquid level of the plasma. The platelet poor plasma was poured off and discarded. The platelet pellet was re-suspended in SRA Wash Buffer 1 (at room temperature) by adding Wash Buffer 1 to the line previously drawn on the tube. To re-suspend the platelet pellet, the contents were gently aspirated and dispensed using disposable pipettes. The re-suspended platelets were incubated for 15 minutes at 37° C. and the tubes were centrifuged at 2400 rpm for 15 minutes. The resulting supernatant was poured off and discarded. The platelet pellet was re-suspended in SRA Wash Buffer 2 by adding the wash buffer to the line previously drawn on the tube. The tubes were inverted, gently aspirated, and dispensed using disposable pipettes to re-suspend the platelet pellet. The tubes were incubated for 45 minutes at 37° C. The platelet suspension was inspected to ensure no clumping or aggregate formation.

Donor Platelets Sample Preparation for Microtiter Plates

Previously screened samples (2 negative and 3 positive) (250 μL) were placed into a clean tube and the tube was capped. The same steps were performed for the Biological QC's (Negative and High). The sample volume of 250 μL was per plate (e.g., two plates required 500 μL of patient sample). The tubes were incubated at 56° C. for 30 minutes and were spun for 10 minutes at 3600 rpm.

For each patient, a set of measurements was prepared by adding the following components to three wells in a row. Into each 1st and 2nd well within a set, 10 μL of low concentration (2.1 IU/mL) heparin was pipetted. Into each 3rd well within a set, 10 μL of high concentration (1050 IU/mL) heparin was pipetted. Then, 20 μL of sample was pipetted into each well, taking care to not draw from the bottom of the tube. For the Negative (i.e., no sample) wells for each donor being tested and for the QC of the plate, Wash Buffer 2 was used.

Prior to pipetting the platelet solution, the quality of the platelet solution was ensured by inverting the tube to gently mix the solution. Prepped platelets (75 μL) for each donor were pipetted into all wells. Each donor tested five patients as an individual and as a pool. The wells were sealed using foil and the plate was placed on a rotating shaker for 60 minutes at room temperature (RT) and a setting of 5. The SRA Stop reagent (100 μL) was added and the wells were sealed using foil. The plate was placed on the rotating shaker for 15 seconds at RT and a setting at 5. The contents were then spun at 3700 rpm for 5 min. The analytical procedure described below was then performed.

Patient Procedure

Platelet Washing Protocol for Patient Samples

Platelets were washed according to the following protocol for donor screening: Blood was drawn from donors into ACD tubes and the tubes were inverted to mix the contents (8-10 mls of platelets~four tubes per plate). The tubes were centrifuged at 1200 rpm for 10 minutes. Platelet rich plasma (PRP) was removed using glass Pasteur Pipettes with a small pipette bulb. Added ACD (111 μL) was added for every mL of plasma. The tubes were inverted to mix the contents. Using 16×100 polypropylene tubes, the PRP tubes were combined after the addition of ACD. The PRP was centrifuged at 2400 rpm for 15 minutes and a line was drawn on the outside of the tube to indicate the liquid level of the plasma. The platelet poor plasma and poured off and discarded. The platelet pellet was re-suspended in SRA Wash Buffer 1 (at room temperature) by adding Wash Buffer 1 to the line previously drawn on the tube. To re-suspend the platelet pellet, the contents were gently mixed by inversion and aspirated. The re-suspended platelets were incubated for 15 minutes at 37° C. and the tubes were centrifuged at 2400 rpm for 15 minutes. The resulting supernatant was poured off and discarded. The platelet pellet was re-suspended in SRA Wash Buffer 2 by adding the wash buffer to the line previously drawn on the tube. The tubes were inverted, gently aspirated, and dispensed to re-suspend the platelet pellet. The tubes were incubated for 45 minutes at 37° C. The platelet suspension was inspected to ensure no clumping or aggregate formation. The platelet solution is stable at room temperature undisturbed for two hours.

Patient Sample Preparation for Microtiter Plates

Patient serum (200 μL) was obtained and placed into a clean tube. The tube was capped. The same steps were performed for the QC sample. The tubes were incubated at 56° C. for 30 minutes and were spun for 10 minutes at 3600 rpm.

For the QC samples, a set of measurements was prepared (0.2, 0.2, and 100) in a microtiter plate. For each patient, the following components were added to four wells in a row. Into each $1^{st}$ well within the set of four, 10 μL of Optima water was pipetted. Into each $2^{nd}$ and $3^{rd}$ well within a set, 10 μL of low concentration (2.1 IU/mL) heparin was pipetted. Into each $4^{th}$ well within a set, 10 μL of high concentration (1050 IU/mL) heparin was pipetted. Then, 20 μL of sample(s) was pipetted into each well, including in the patient wells and biological QC wells, taking care to not draw from the bottom of the tube. For the Negative (i.e., no sample) wells, Wash Buffer 2 was used in place of the 20 μL patient sample.

Prior to pipetting the platelet solution, the quality of the platelet solution was ensured by inverting the tube to gently mix the solution. Wash Buffer 2 (75 μL) was pipetted into the first well of the patient samples set. Platelet solution (75 μL) was pipetted into all other wells. The wells were sealed using foil and placed on a rotating shaker for 60 minutes at room temperature (RT) and a setting of 5. The SRA Stop reagent (100 μL) was added and the wells were sealed using foil. The plate was placed on the rotating shaker for 15 seconds at RT and a setting at 5. The contents were then spun at 3700 rpm for 5 min. The analytical procedure described below was then performed.

Analytical Procedure

The tubes of platelet solution were gently mixed by inverting the tubes. The blanks, calibrators, quality controls, and platelet solutions (100 μL each) were pipetted into the appropriate wells. Sample (100 μL) was removed from the Microtiter plate and added to the 96-deep well plate. For double blanks, 100 μL of blank matrix and 300 μL of acetonitrile were added. Then, 300 μL of 200 ng/mL serotonin-d4 in acetonitrile was added. The contents were vortexed at 2500 rpm for 10 minutes and centrifuged for 10 minutes at 3700 rpm. The contents (150 μL) were then transferred to a clean plate. Ethyl acetate (150 μL) was added to all wells. The plate was sealed with foil, vortexed at 2500 rpm for 10 seconds, and centrifuged for 15 seconds at 3700 rpm. The resulting sample (20 μL) was injected on the LC-MS/MS system for LC-MS/MS analysis.

Biological QC Sample Prep for Microtiter Plate

Patient samples (200 μL) were obtained, placed into clean tube, and the tube was capped. The same steps were performed for the Biological QC's (Negative and High). The tubes were incubated at 56° C. for 30 minutes and spun for 10 minutes at 3600 rpm. A set of measurements was prepared for the same patient by using three wells. Into each 1st and 2nd well within a set, 10 μL of low concentration (2.1 IU/mL) heparin was pipetted. Into each 3rd well within a set, 10 μL of High concentration (1050 IU/mL) heparin was pipetted. Then, 20 μL of sample was pipetted into each well.

The tubes of platelet solution were gently mixed by inverting the tubes. Prepped platelets (75 μL) were pipetted into all wells. The wells were sealed with foil and placed on a rotating shaker for 60 minutes at room temperature and a setting of 5. The SRA Stop Reagent (100 μL) was added and the plate was sealed with foil. The plate was placed on a rotating shaker for 15 seconds at RT and a setting at 5 and was spun at 3700 rpm for 5 min.

Reporting Results

Units for this assay are in Percent Release (% release). The percent release is calculated using total serotonin in platelets and serotonin release in the presence of patient serum and donor platelets. Specifically, the percent release is the ratio of serotonin release in the presence of patient samples and donor platelets divided by the total amount of serotonin or labeled serotonin in the donor platelets used in the assay.

Results are reported as a percent release of the 0.2 IU/mL and the 100 IU/mL.

The lower limit of quantification (LLOQ) for this assay is 1 ng/mL. The upper limit of quantification (ULOQ) is 1000 ng/mL. If sufficient specimen is not available to repeat, "QNSR" is indicated. This abbreviation notifies the account that there is insufficient specimen to verify results.

Results Interpretation

The results were interpreted based on the serotonin percent release values for the low dose heparin assay (i.e., Low Heparin Percent Release or Low Release) and for the high dose heparin assay (i.e., High Heparin Percent Release or High Release). The interpretations based on Low and High Heparin Percent Release are displayed in tabular form in Table 1 and graphically in FIG. 2.

TABLE 1

SRA Interpretation Table

| Low Heparin Percent Release | High Heparin Percent Release | SRA Result |
|---|---|---|
| 0-20 | Disregard | Negative |
| 21-30 | 0-20 | Low Positive |
| 31-40 | 0-20 | Positive |
| >40 | ≤(Low Heparin × 0.5) | Positive |
| 21-40 | >20 | Indeterminate |
| >40 | >(Low Heparin × 0.5) | Indeterminate |

As shown in Table 1 and as depicted in FIG. 2, if the serotonin percent release value for the low dose heparin assay was 20 percent or less, the interpretation was negative, regardless of the result of the high dose heparin assay. In all cases where the serotonin percent release value for the low dose heparin assay was greater than 20 percent, the relationship between the serotonin percent release values for the low dose heparin assay and for the high dose heparin assay was used to determine the interpretation. For all possible serotonin percent release values for the low dose heparin assay, the corresponding Positive versus Indeterminate threshold was also tabulated. If the result of the high release assay was less than or equal to the number tabulated, the interpretations were either "Low Positive" (Low Release 21-30%) or "Positive" (Low Release>30%). If the result of the high release assay was greater than the number tabulated for a measured low release assay, the interpretation was "Indeterminate".

Negative Result

As stated above, when the Low Heparin Percent Release was from 0-20%, the SRA result was "negative." While these results argue against a diagnosis of heparin-induced-thrombocytopenia (HIT), they do not completely exclude the diagnosis. The result should be interpreted in conjunction with other HIT assays, and the context of all the clinical information including the platelet count, the type of heparin administered, the duration of heparin exposure, previous heparin exposure, and any thrombotic history. The assay measures serotonin release from donor platelets in the presence of patient's serum and heparin. A positive result requires >20% release in the presence of low dose (0.2 IU/mL) heparin and inhibition of serotonin release in the presence of high dose (100 IU/mL) heparin.

Low Positive Result

When the Low Heparin Percent Release was from 21-30% and the High Heparin Percent Release was from 0-20%, the SRA result was "low positive." While these results are positive and would support a diagnosis of heparin-induced-thrombocytopenia (HIT), they fall just above the cut-off and should be interpreted in conjunction with other HIT assays and the context of all the clinical information including the platelet count, the type of heparin administered, the duration of heparin exposure, previous heparin exposure and any thrombotic history. The assay measures serotonin release from donor platelets in the presence of patient's serum and heparin. A low positive result consists of a 21-30 percent release in the presence of low dose (0.2 IU/mL) heparin and inhibition of serotonin release in the presence of high dose (100 IU/mL) heparin.

Positive Result

When the Low Heparin Percent Release was from 31-40% and the High Heparin Percent Release was from 0-20%, the SRA result is "positive." Additionally, when the Low Heparin Percent Release was greater than 40% (i.e., >40%) and the High Heparin Percent Release was less than or equal to the Low Heparin Percent Release multiplied by 0.5 (i.e., ≤(Low Heparin Percent Release×0.5)), the SRA result was "positive." The patient's serum tested positive by SRA and supports a diagnosis of heparin-induced-thrombocytopenia (HIT). The assay measures serotonin release from donor platelets in the presence of patient's serum and heparin. A positive result requires greater than 20% release in the presence of low dose (0.2 IU/mL) heparin and inhibition of release in the presence of high dose (100 IU/mL) heparin. The result should be interpreted in conjunction with other HIT assays, and the context of all the clinical information including the platelet count, the type of heparin administered, the duration of heparin exposure, previous heparin exposure and any thrombotic history.

Indeterminate Result

When the Low Heparin Percent Release was from 21-40% and the High Heparin Percent Release was greater than 20% (i.e., >20%), the SRA result was "indeterminate." Additionally, when the Low Heparin Percent Release was greater than 40% (i.e., >40%) and the High Heparin Percent Release was greater than the Low Heparin Percent Release multiplied by 0.5 (i.e., >(Low Heparin Percent Release× 0.5)), the SRA result was "indeterminate." The assay measures serotonin release from donor platelets in the presence of patient's serum and heparin. A positive result requires greater than 20% release in the presence of low dose (0.2 IU/mL) heparin and inhibition of release in the presence of high dose (100 IU/mL) heparin. Although there was greater than 20% serotonin release in the presence of low dose heparin, this reaction was not adequately inhibited by high dose heparin. While these results are not consistent with a diagnosis of heparin-induced-thrombocytopenia (HIT), they do not completely exclude the diagnosis. The result should be interpreted in conjunction with other HIT assays, and the context of all the clinical information including the platelet count, the type of heparin administered, the duration of heparin exposure, previous heparin exposure and any thrombotic history. This reaction complex could be due to circulating immune complexes, high titer HLA class-1 antibodies and/or other platelet activating factors.

Example 2

Positive HIT Determination

Figure 3:
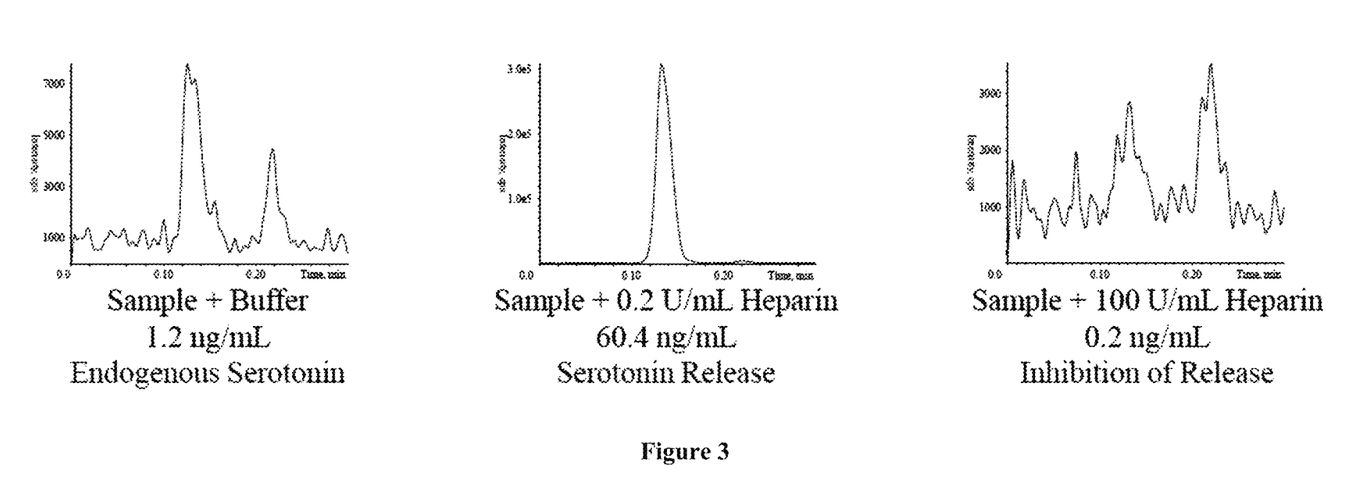
FIG. 3 shows chromatograms for the serotonin release assays described herein that resulted in a positive HIT determination. The left panel shows endogenous serotonin; the middle panel shows serotonin release at 0.2 U/mL heparin; and the right panel shows serotonin release at 100 U/mL heparin.

A biological sample was tested for HIT according to the procedure in Example 1. The sample showed a 27% serotonin release with 0.2 U/mL heparin and inhibition of release at 100 U/mL heparin (see FIG. 3), relative to the total serotonin (100%) available within the platelets determined through analysis according to the methods described herein without the addition of a biological sample. As shown in FIG. 3, top left panel, the endogenous serotonin level in the biological sample and buffer is 1.2 ng/mL. The top middle panel of FIG. 3 shows the biological sample and 0.2 U/mL heparin. Approximately 60.4 ng/mL of serotonin was measured in the sample. The top right panel of FIG. 3 shows the biological sample and 100 U/mL heparin. Approximately 0.2 ng/mL of serotonin was measured in the sample. The percent serotonin release in the sample and 0.2 U/mL heparin was 27%. The biological sample was determined to be positive for HIT.

Figure 4:
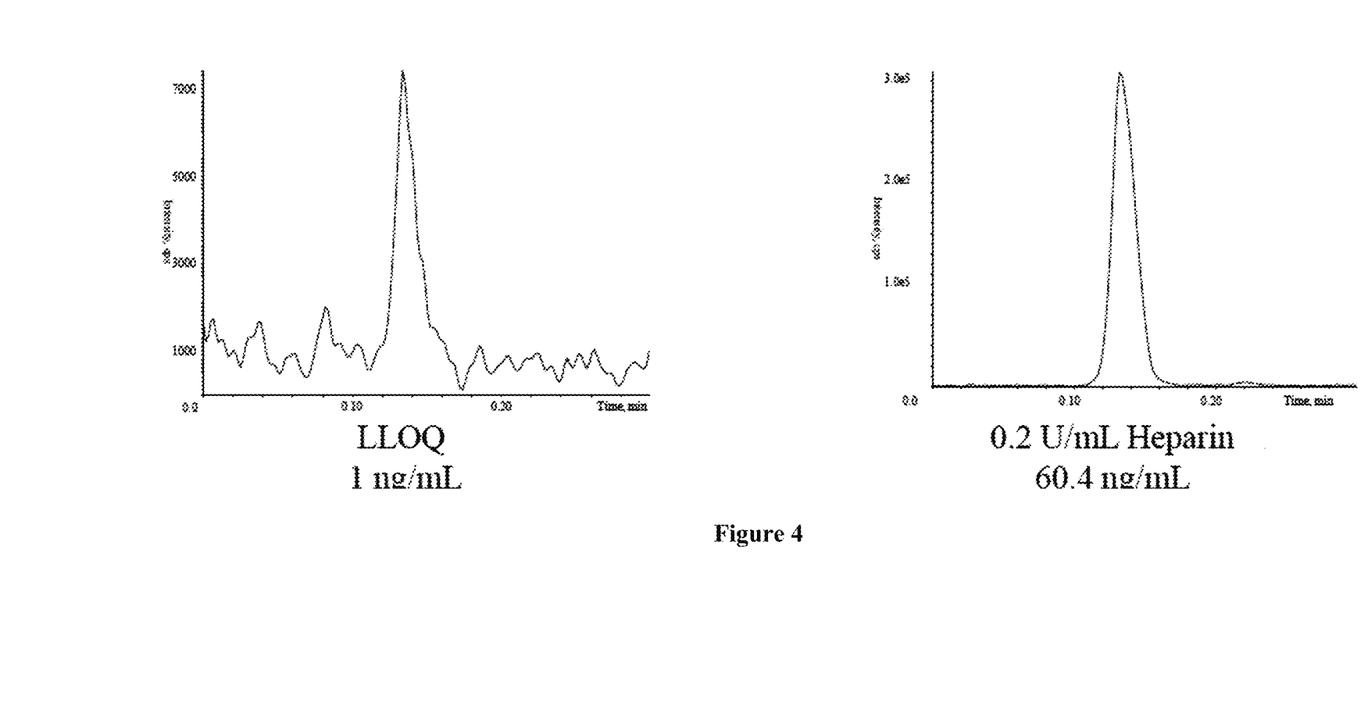
FIG. 4 shows chromatograms comparing the lower limit of quantification (LLOQ) for the assay (left side) to the positive release sample (right side).

The positive release chromatogram, where 60.4 ng/mL of serotonin was present, was compared to the LLOQ chromatogram, where 1 ng/mL of serotonin was present. As shown in FIG. 4, the assay is capable of detecting serotonin at levels as low as 1 ng/mL.

Example 3

Transition Ratio Assessment

Transition ratio assessments were performed by dividing the area response of the qualifying transition by the area response of the quantifying transition (i.e., transition ratio) in a sample and comparing that to the average transition ratio measured in calibrators from the same batch (excluding calibrator 1). Data for transition ratio assessment was compiled from the quantitated results table. Acceptance criteria established during validation were provided for the analyte (see Table 2). In the event that concentration-specific acceptance criteria cannot be utilized in an automated fashion, recommended acceptance criteria for all samples (i.e., concentration independent) were provided as a back-up.

TABLE 2

Recommended Acceptance Criteria for Transition Ratio Monitoring

| Analyte | Quantifying Transition | Qualifying Transition | Transition Ratio | Level | Tolerance (% Bias) |
|---|---|---|---|---|---|
| Serotonin | 160.1/115.1 | 160.1/89.1 | 0.278 | 1-10 ng/mL | ±30% |
| | | | | 10-1000 ng/mL | ±15% |

TABLE 2-continued

Recommended Acceptance Criteria for Transition Ratio Monitoring

| Analyte | Quantifying Transition | Qualifying Transition | Transition Ratio | Level | Tolerance (% Bias) |
|---|---|---|---|---|---|
| Serotonin IS | 164.1/118.1 | 164.1/136.1 | 0.303 | N/A | N/A |

The invention claimed is:

1. A method for determining amount of serotonin released by a biological sample, the method comprising:
   incubating at least one sample comprising the biological sample, heparin and donor platelets for a period of time to release serotonin from the donor platelets, thereby generating at least one incubated sample;
   chromatographically separating serotonin from other components in the at least one incubated sample using liquid chromatography; and
   analyzing the chromatographically separated serotonin by tandem mass spectrometry to determine the amount of released serotonin in the at least one sample relative to a total amount of serotonin available in the donor platelets.

2. The method of claim 1, wherein the analyzing includes ionizing the chromatographically separated serotonin using electrospray ionization, atmospheric pressure chemical ionization, or atmospheric pressure photoionization.

3. The method of claim 1, wherein the tandem mass spectrometry uses a quadrupole mass spectrometer.

4. The method of claim 3, wherein the quadrupole mass spectrometer is a triple quadrupole mass spectrometer.

5. The method of claim 4, wherein the analyzing includes:
   detecting intact serotonin ion in first quadrupole;
   fragmenting the intact serotonin ion in second quadrupole to yield one or more serotonin fragment ions; and,
   detecting the one or more serotonin fragment ions in third quadrupole.

6. The method of claim 1, wherein the analyzing comprises ionizing the chromatographically separated serotonin to produce one or more serotonin ions, comprising at least one of a precursor ion of 160.1±0.5 mass-to-charge ratio, or a product ion of 115.1±0.5, 132.1±0.5, 105.1±0.5, or 89.1±0.5 mass-to-charge ratio.

7. The method of claim 1, wherein the at least one sample is at least two samples, wherein a first one or more of the at least two samples comprises heparin at a first concentration, and a second one or more of the at least two samples comprises heparin at a second concentration different from the first concentration.

8. The method of claim 7, wherein the first concentration of heparin is 0.001 to 1 U/mL, and the second concentration of heparin is 50 to 1000 U/mL.

9. The method of claim 1, wherein the biological sample is a serum sample or a plasma sample.

10. The method of claim 9, wherein the serum sample or the plasma sample is obtained from a heparin-treated subject, or a subject suspected of having heparin-induced thrombocytopenia (HIT).

11. The method of claim 1, wherein the donor platelets are washed and partially purified prior to the incubating the at least one sample.

12. The method of claim 1, wherein the donor platelets are serotonin-incubated donor platelets.

13. The method of claim 12, wherein the serotonin-incubated donor platelets are incubated with serotonin prior to the incubating the at least one sample.

14. The method of claim 12, wherein the serotonin-incubated donor platelets are incubated with stable isotopically-labeled serotonin prior to the incubating the at least one sample.

15. The method of claim 1, further comprising partially purifying the at least one incubated sample prior to the chromatographically separating serotonin from the other components in the at least one incubated sample.

16. The method of claim 1, wherein the liquid chromatography includes reverse phase column chromatography.

17. The method of claim 1, wherein the liquid chromatography includes using two or more liquid chromatography columns in parallel, where the two or more liquid chromatography columns are connected inline to a single mass spectrometer.

18. A system for determining amount of serotonin released by a biological sample, the system comprising:
a station for incubating at least-one sample comprising the biological sample, heparin and donor platelets for a period of time to release serotonin from the donor platelets, thereby generating at least one incubated sample;
a station for chromatographically separating serotonin from other components in the at least one incubated sample using liquid chromatography; and
a station for analyzing the chromatographically separated serotonin by tandem mass spectrometry to determine amount of released serotonin in the at least one sample relative to a total amount of serotonin available within the donor platelets.

19. The system of claim 18, wherein the station for analyzing the chromatographically separated serotonin by tandem mass spectrometry comprises a quadrupole mass spectrometer.

20. The system of claim 19, wherein the quadrupole mass spectrometer is a triple quadrupole mass spectrometer.

21. The system of claim 18, wherein the station for chromatographically separating serotonin comprises at least one reverse phase column.

22. The system of claim 18, wherein the station for chromatographically separating serotonin comprises two or more liquid chromatography columns in parallel, wherein the two or more liquid chromatography columns are connected inline to a single mass spectrometer.

23. The system of claim 18, further comprising a station for partially purifying the at least one incubated sample prior to chromatographically separating serotonin from other components in the at least one incubated sample.

24. The system of claim 18, wherein the at least one sample is at least two samples, wherein a first one or more of the at least two samples comprises heparin at a first concentration, and a second one or more of the at least two samples comprises heparin at a second concentration different from the first concentration.

25. The system of claim 24, wherein the first concentration of heparin is 0.001 to 1 U/mL, and the second concentration of heparin is 50 to 1000 U/mL.

* * * * *